United States Patent
Park et al.

(10) Patent No.: US 7,423,438 B2
(45) Date of Patent: Sep. 9, 2008

(54) METHOD AND APPARATUS FOR MEASURING BODY FAT BY USING BIOELECTRICAL IMPEDANCE

(75) Inventors: Kun-kook Park, Yongin-si (KR); Kyung-Ho Kim, Yongin-si (KR); Jeong-Je Park, Yongin-si (KR)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

(21) Appl. No.: 11/942,321

(22) Filed: Nov. 19, 2007

(65) Prior Publication Data

US 2008/0071187 A1 Mar. 20, 2008

Related U.S. Application Data

(62) Division of application No. 11/242,899, filed on Oct. 5, 2005, now Pat. No. 7,317,320.

(30) Foreign Application Priority Data

Nov. 6, 2004 (KR) .................. 10-2004-0090126

(51) Int. Cl.
*G01R 27/08* (2006.01)
*A61B 5/05* (2006.01)
(52) U.S. Cl. .................. 324/696; 324/713; 324/715; 600/547
(58) Field of Classification Search .................. 324/696, 324/713, 715; 600/547
See application file for complete search history.

(56) References Cited

U.S. PATENT DOCUMENTS

| 6,188,925 | B1 | 2/2001 | Kawanishi et al. |
| 6,509,748 | B1 | 1/2003 | Cheng |
| 6,551,257 | B1 * | 4/2003 | Sunako ............... 600/587 |
| 6,906,533 | B1 | 6/2005 | Yoshida |
| 2005/0228449 | A1 * | 10/2005 | Koyama ............... 607/1 |

* cited by examiner

*Primary Examiner*—Diego Gutierrez
*Assistant Examiner*—Amy He
(74) *Attorney, Agent, or Firm*—Sughrue Mion, PLLC

(57) ABSTRACT

Provided are a method and apparatus for measuring body fat using current electrodes and voltage electrodes. The method includes continually detecting a voltage drop across the voltage electrodes by smoothly raising a contact pressure applied to the electrodes; determining a threshold contact pressure with reference to the detected voltage drop depending on variation of the contact pressure, the voltage drop across the voltage electrodes not increasing under the threshold contact pressure even when the contact pressure increases; comparing a detected contact pressure with the threshold contact pressure; detecting a measurement voltage across the voltage electrodes only when the detected contact pressure is larger than the threshold contact pressure; and compensating the measurement voltage for a threshold contact voltage corresponding to the threshold contact pressure and calculating a body fat value corresponding to the compensated measurement voltage.

4 Claims, 9 Drawing Sheets

| CONTACT AREA : | LARGE | SMALL |
| CONTACT PRESSURE : | LARGE | SMALL |
| CONTACT VOLTAGE : | LARGE | SMALL |
| BODY FAT VALUE : | LARGE (ex. 23%) | SMALL (ex. 21%) |

METHOD AND APPARATUS FOR MEASURING BODY FAT BY USING BIOELECTRICAL IMPEDANCE

CROSS REFERENCE OF RELATED APPLICATION

This application is a divisional application of U.S. application Ser. No. 11/242,899 filed Oct. 5, 2005, now U.S. Pat. No. 7,317,320 which claims priority from Korean Patent Application No. 10-2004-0090126 filed Nov. 6, 2004, in the Korean Intellectual Property Office, the entire disclosure of which is incorporated herein by reference.

BACKGROUND OF THE INVENTION

The present invention relates to an apparatus for measuring body fat by using biomedical impedance, and more particularly, to a method of and an apparatus for measuring body fat, by which measurement errors can be reduced and repeatability can be improved by compensating for variation of a contact voltage caused by variation of an electrode contact area.

DESCRIPTION OF RELATED ART

A body fat value serves as a main index to determine fatness, which is known to cause many adult diseases. As interest in fatness is increasing and the necessity of measuring body fat is increasing, a body fat measurement apparatus is becoming pervasive.

Today, a method of measuring bioelectrical impedance is most frequently used to measure body fat. This method is based on the fact that bioelectrical impedance varies depending on the amount of body fat.

Typically, since fat occupies 17% of a human body and contains little water, the bioelectrical impedance of a human body varies depending on the amount of body fat. Therefore, it is possible to measure the amount of body fat by detecting the bioelectrical impedance of a human body.

A typical body fat measurement apparatus is a four-electrode type having two current electrodes and two voltage electrodes. The four electrodes usually make contact with parts of a human body, for example, the hands. In the typical body fat measurement apparatus, the two current electrodes are used to apply a constant current through a human body, and the two voltage electrodes are used to measure a voltage drop caused by the constant current. The voltage drop across the voltage electrodes is proportional to the bioelectrical impedance of a human body.

FIG. 1 schematically illustrates an example of a portable body fat measurement apparatus. The portable body fat measurement apparatus has a display unit mounted on a front surface of a chassis, an operation unit, and measurement electrodes mounted on both sides of the chassis. As shown in FIG. 1, the four electrodes are mounted on the left and right sides, two by two, respectively. For example, the voltage electrodes are mounted on the front left side and the front right side, and the current electrodes are mounted on the rear right side and the rear left side.

FIG. 2 schematically illustrates a principle of measuring body fat by using a four-electrode type body fat measurement apparatus. Two current electrodes 102a, 102b are connected to a constant current source 104, and two voltage electrodes 106a, 106b are connected to a voltage meter 108. When fingers of the left and right hands make contact with the current electrodes 102a, 102b, respectively, the constant current applied from the constant current source 104 flows through the right hand, the upper-half of a human body, and the left hand. As a result, a voltage drop V occurs due to the bioelectrical impedance of a human body. The voltage drop V is proportional to a body fat ratio. Then, the voltage drop V caused by the impedance of a human body is measured by using the voltage meter 108 through the voltage electrodes 106a, 106b making contact with the fingers of the left and right hands of a user.

Subsequently, a user inputs personal information such as the height, weight, age, and sex of a user, into the body fat measurement apparatus, and the voltage measured by the voltage meter 108 is input to a predetermined calculation function to calculate the amount of body fat. Finally, the measurement result is displayed on the display unit.

Therefore, it is considered that the measurement accuracy depends on the user's posture, contact areas with the measurement electrodes, and the like. Particularly, for a portable body fat measurement apparatus, it is recommended that the fingers be spread out as much as possible and the user's posture be stabilized as shown in FIG. 1.

In the meantime, the contact area means the area over which a user makes contact with the measurement electrodes, i.e., the voltage electrodes 106a, 106b. Experimental observation has shown that variation of the contact area significantly affects the measurement result. Such variation of the contact area alters the contact voltage between a human body and the voltage electrodes, and thus the variation of the contact voltage alters the voltage measured from the voltage electrodes 106a, 106b. It is considered that the contact area of the measurement electrode is proportional to the finger contact pressure applied when the measurement electrode is pressed.

FIG. 3 schematically illustrates variation of a body fat value depending on the contact area. The left of FIG. 3 shows a situation where the contact area is sufficiently large, and the right of FIG. 3 shows a situation where the contact is smaller than that. Referring to the left of FIG. 3, if the contact area, i.e., the contact pressure, of a user increases, the contact voltage correspondingly increases, so that the measurement body fat value is measured to be larger. On the other hand, if the contact area, i.e., the contact pressure, of a user decreases, the contact voltage correspondingly decreases, so that the measurement body fat value is measured to be smaller.

Also, it has been observed that such a measurement deviation caused by the variation of the contact area reaches about ±2% of the true body fat value. This means that a person having a weight of 64 Kg would have a deviation of ±1.2 Kg.

Since the contact area may change for every measurement, it is necessary to compensate for such variation of the contact area. Otherwise, measurement consistency of the body fat measurement apparatus cannot be ensured. In other words, if the variation of the contact area occurs, repeatability cannot be guaranteed even when conditions other than the contact area are sufficiently satisfied.

SUMMARY OF THE INVENTION

An aspect of the present invention is to provide a method of measuring body fat, by which few errors occur, and reliable repeatability can be attained by compensating for the measurement deviation caused by the variation of the contact area.

Also, an aspect of the present invention provides an apparatus for measuring body fat using the aforementioned method.

According to an aspect of the present invention, there is provided a method of measuring body fat by using current electrodes for applying a constant current in a human body and voltage electrodes for detecting a voltage drop caused by bioelectrical impedance of the human body, the method comprising: detecting a voltage across the voltage electrodes under a first conditional pressure and a second conditional pressure to obtain a first conditional voltage and a second conditional voltage; determining the conditional pressures, a difference between the conditional pressures, the conditional voltages, and a difference between the conditional voltages and storing the conditional pressures, the difference between the conditional pressures, the conditional voltages, and the difference between the conditional voltages in a memory; detecting a measurement voltage under an arbitrary pressure; performing interpolation by using the conditional pressures, the difference between the conditional pressures, the conditional voltages, the difference between the conditional voltages, and the arbitrary pressure to obtain a contact voltage; and compensating the measurement voltage for the contact voltage to calculate a body fat value corresponding to the compensated measurement voltage.

According to another aspect of the present invention, there is provided a method of measuring body fat by using current electrodes for applying a constant current in a human body and voltage electrodes for detecting a voltage drop caused by bioelectrical impedance of the human body, the method including: continually detecting a voltage drop across the voltage electrodes by smoothly raising a contact pressure applied to the electrodes; determining a threshold contact pressure with reference to the detected voltage drop depending on variation of the contact pressure, the voltage drop across the voltage electrodes not increasing under the threshold contact pressure even when the contact pressure increases; comparing a detected contact pressure with the threshold contact pressure; detecting a measurement voltage across the voltage electrodes only when the detected contact pressure is larger than the threshold contact pressure; and compensating the measurement voltage for a threshold contact voltage corresponding to the threshold contact pressure and calculating a body fat value corresponding to the compensated measurement voltage.

According to still another aspect of the present invention, there is provided a method of measuring body fat by using current electrodes for applying a constant current in a human body and voltage electrodes for detecting a voltage drop caused by bioelectrical impedance of the human body, the method including: continually detecting a voltage drop across the voltage electrodes by smoothly raising a contact pressure applied to the electrodes; determining a threshold contact pressure with reference to variation of the detected voltage drop depending on the contact pressure, the voltage drop across the voltage electrodes not increasing under the threshold contact pressure even when a user increases the contact pressure; selecting two conditional contact pressures in a linear range in which variation of the contact voltage with respect to the contact pressure shows linearity; determining the threshold contact pressure, the conditional contact pressures, a difference between the conditional contact pressures, conditional voltages detected under the conditional contact pressures, and a difference between the conditional voltages and storing the difference between the conditional contact pressures, the conditional voltages, and the difference between the conditional voltages in a memory; detecting a measurement voltage under an arbitrary contact pressure; comparing the arbitrary contact pressure with the threshold contact pressure; performing interpolation by using the threshold contact pressure, the conditional contact pressures, the difference between the conditional contact pressures, the conditional voltages detected under the conditional contact pressures, the difference between the conditional voltages, and the arbitrary contact pressure to obtain a contact voltage if the arbitrary contact pressure is smaller than the threshold contact pressure; compensating the measurement voltage for a threshold contact voltage corresponding to the threshold contact pressure if the arbitrary contact pressure is larger than the threshold contact pressure; and calculating a body fat value corresponding to the compensated measurement voltage.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF EXEMPLARY EMBODIMENTS OF THE INVENTION

Hereinafter, exemplary embodiments consistent with the present invention will be described in detail with reference to the accompanying drawings.

Figure 4A:
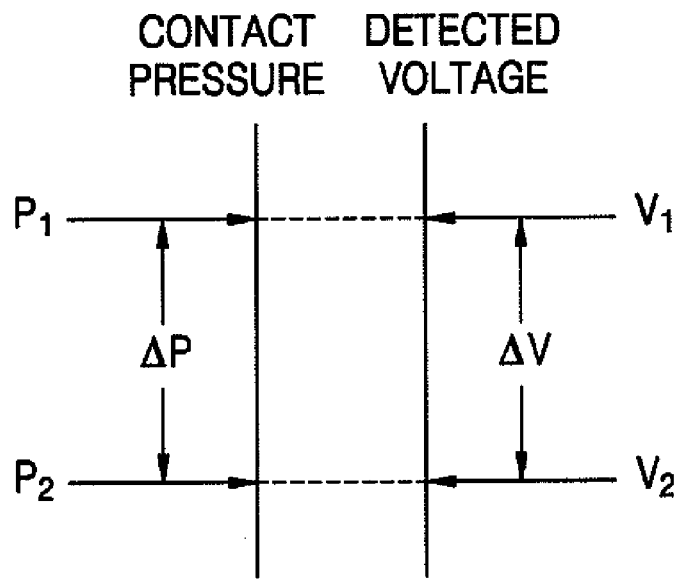
FIGS. 4A and 4B schematically illustrate a principle of measuring body fat according to a first exemplary embodiment of the present invention.
Figure 4B:
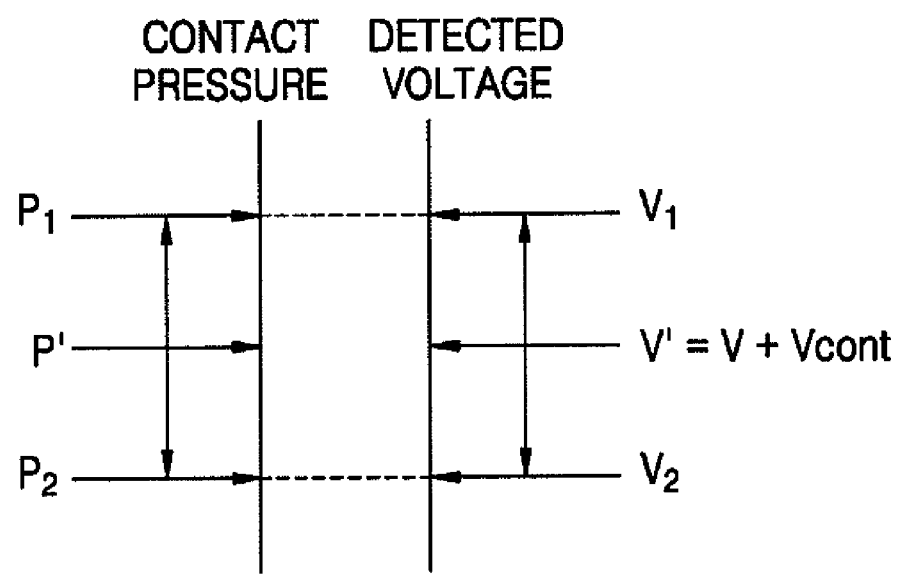

FIGS. 4A and 4B schematically illustrate a principle of measuring body fat according to the first embodiment of the present invention. In FIG. 4A, assuming that V1 denotes a voltage drop across the voltage electrodes in a first conditional pressure P1, and V2 denotes a voltage drop across the voltage electrodes measured in a second conditional pressure P2, a measurement voltage V' in an arbitrary pressure P' can be obtained by interpolation using a voltage difference ΔV between the conditional voltages V1 and V2 and a pressure difference ΔP between the conditional pressures P1 and P2.

More specifically, the pressure difference ΔP between the conditional pressures P1 and P2 can be regarded as part of a variation range of the contact pressure, and the voltage difference ΔV between the conditional voltages V1 and V2 can be regarded as part of a variation range of the contact voltage caused by the contact pressure. As mentioned above, the contact voltage is proportional to the contact pressure. Therefore, a measurement voltage V' in an arbitrary contact pressure P' can be obtained by interpolation using the pressure difference ΔP between the conditional pressures P1 and P2 and the voltage difference ΔV between the conditional voltages V1 and V2. By the interpolation, the measurement voltage V' can be obtained when the arbitrary contact pressure P' exceeds the conditional pressure P1 or P2 as well as when the arbitrary contact pressure P' falls between the conditional pressures P1 and P2.

Assuming that V' denotes a measurement voltage measured when an arbitrary contact pressure P' is applied, V' can be considered as a sum of the voltage caused by the human body impedance and the contact voltage Vcont. Therefore, it is possible to extract the human body impedance by compensating the measurement voltage V' for the contact voltage Vcont. Here, the contact voltage Vcont can be obtained by applying interpolation with the conditional pressures P1 and P2, the difference ΔP between the conditional contact pressures P1 and P2, the conditional voltages V1 and V2, the difference ΔV between the conditional voltages V1 and V2, and the arbitrary pressure P'.

Figure 5:
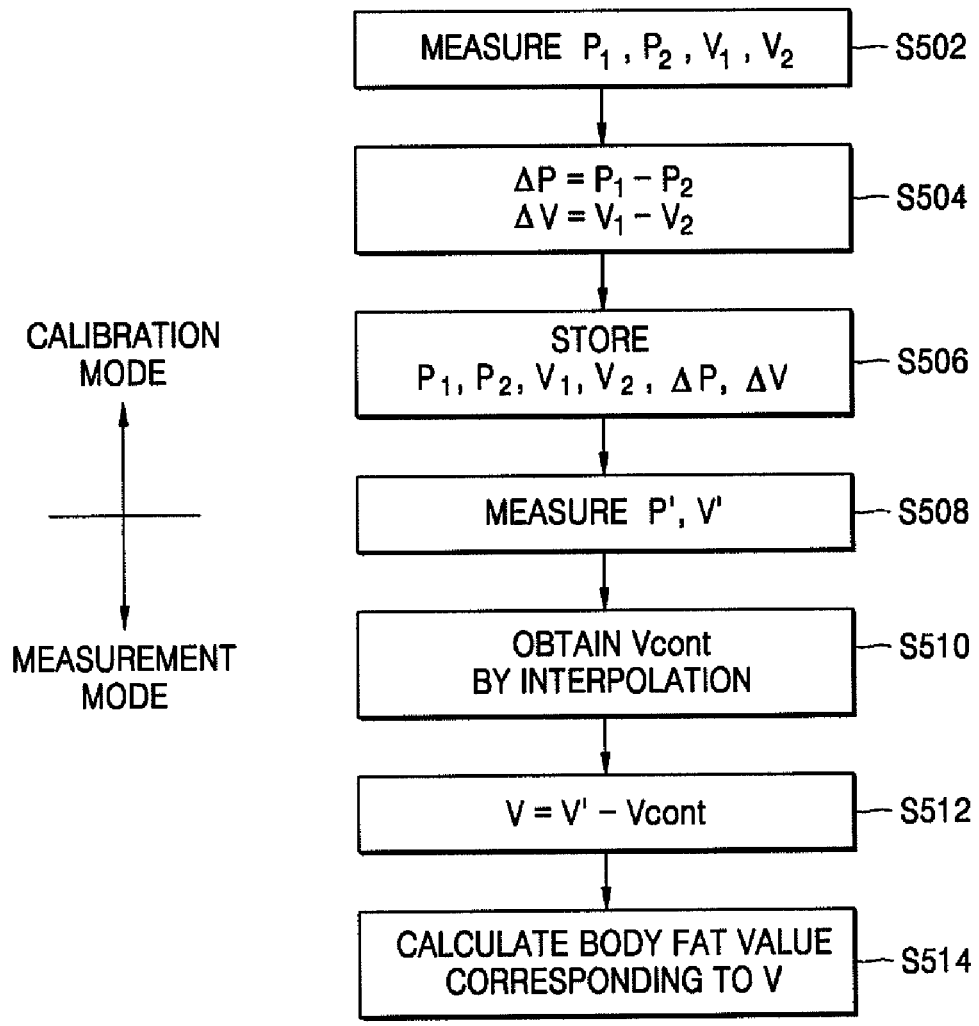
FIG. 5 is a flowchart illustrating a method of measuring body fat according to the first embodiment of the present invention.

FIG. 5 is a flowchart illustrating a method of measuring body fat according to the first embodiment of the present invention.

The first conditional voltage V1 and the second conditional voltage V2 are detected in the first conditional contact pressure P1 and the second conditional contact pressure P2, respectively (S502).

Then, the difference ΔP between the conditional contact pressures P1 and P2 and the difference ΔV between the detected conditional voltages V1 and V2 are obtained (S504).

The conditional contact pressures P1 and P2, the difference ΔP between the conditional contact pressures P1 and P2, the conditional voltages V1 and V2, and the difference ΔV between the conditional voltages V1 and V2 are stored in a memory (S506).

A voltage V' is detected in an arbitrary contact pressure P'(S508).

The contact voltage Vcont is obtained by using the conditional contact pressures P1 and P2, the difference ΔP between the conditional contact pressures P1 and P2, the conditional voltages V1 and V2, and the difference ΔV between the conditional voltages V1 and V2 stored in operation S506, and the arbitrary pressure P' (S510).

Then, the detected voltage V' is compensated for the obtained contact voltage Vcont (S512).

The body fat value corresponding to the compensated measurement voltage (V=V'−Vcont) is calculated (S514).

The body fat value is calculated by entering personal information such as height, weight, age, and sex of a user and the compensated measurement voltage V into a particular calculation function.

The procedures S502 through S506 for obtaining the conditional pressures P1 and P2, the difference ΔP between the conditional pressures P1 and P2, the conditional voltages V1 and V2, and the difference ΔV between the conditional voltages V1 and V2 are performed to calibrate the body fat measurement apparatus for a user.

Figure 6:
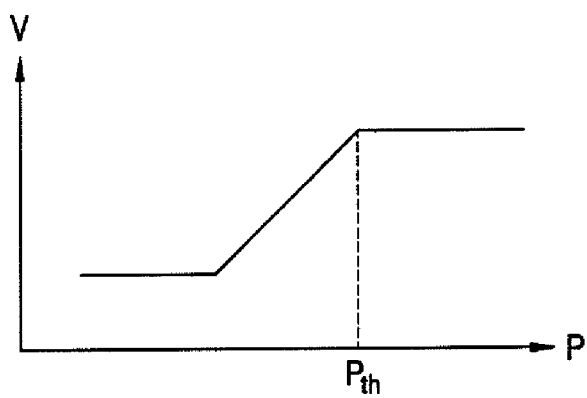
FIG. 6 schematically illustrates a principle of measuring body fat according to a second exemplary embodiment of the present invention.

FIG. 6 schematically illustrates a principle of measuring body fat according to the second embodiment of the present invention, which shows variation of the contact voltage depending on the contact pressure. Referring to FIG. 6, the contact voltage initially increases as the contact pressures increase. However, at a particular threshold contact pressure Pth, the contact voltage does not increase any more (i.e., the contact voltage is saturated). This is because the contact area does not increase due to characteristics of a human body when the contact pressure exceeds the threshold value Pth. For this reason, since the contact voltage is saturated after the contact pressure exceeds the threshold value Pth, it is possible to obtain a voltage drop caused by only the human body impedance by compensating the obtained measurement voltage for the threshold contact voltage Vth corresponding to the threshold contact pressure Pth when a user retains his contact pressure above the threshold contact pressure. Here, the threshold contact voltage Vth corresponding to the threshold contact pressure Pth can be experimentally and statistically determined.

Figure 7:
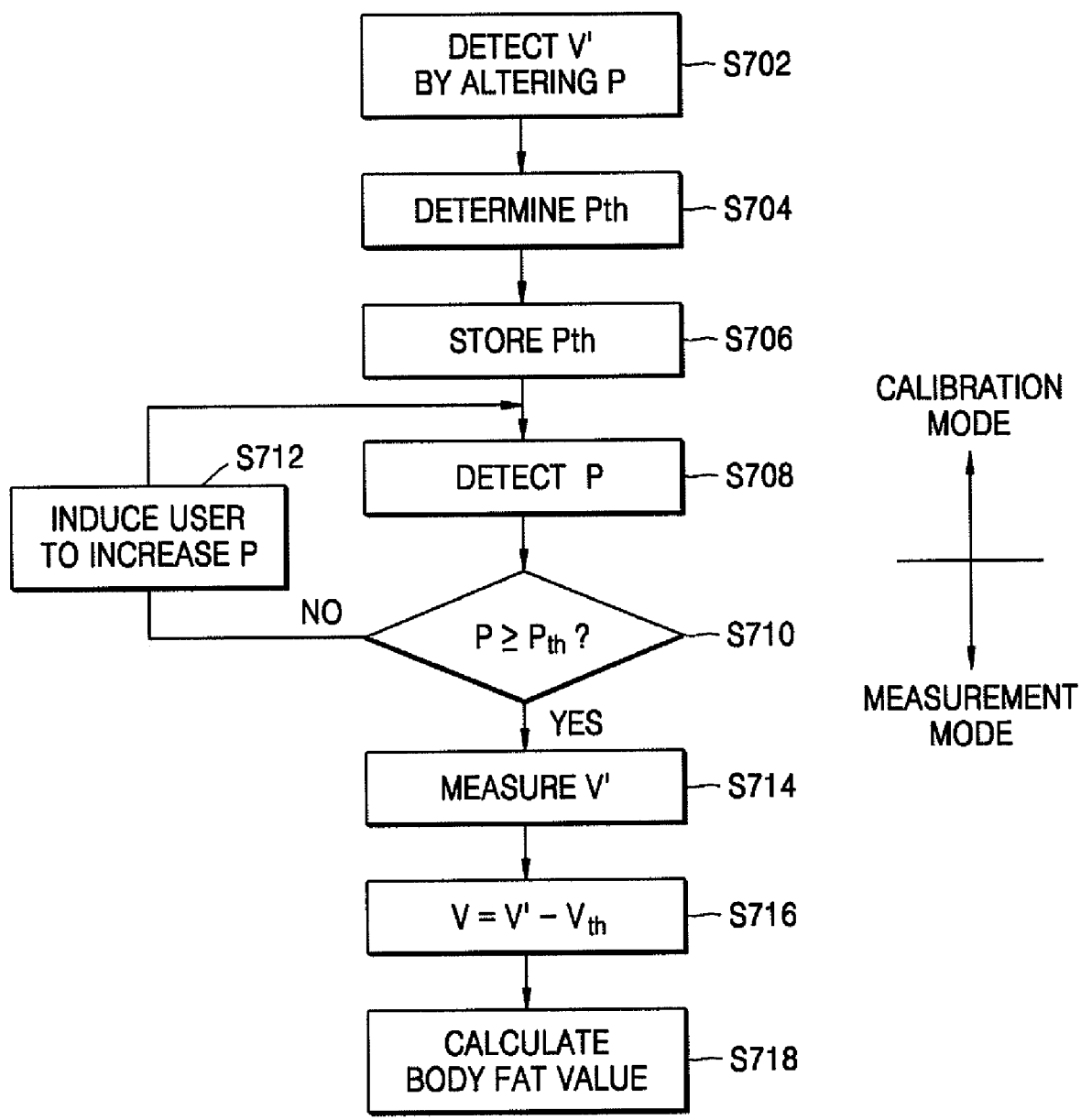
FIG. 7 is a flowchart illustrating a method of measuring body fat according to the second embodiment of the present invention.

FIG. 7 is a flowchart illustrating a method of measuring body fat according to the second embodiment of the present invention.

First, in a calibration mode, the voltage drop V' across the voltage electrodes is continuously measured by smoothly raising the contact pressure (S702).

Then, a graph such as that shown in FIG. 6 is obtained by referring to variation of the contact voltage V depending on the contact pressure P, and the threshold contact pressure Pth is determined (S704).

The obtained threshold contact pressure Pth is stored in a memory (S706).

The obtained threshold contact pressure Pth is used to determine a proper measurement time point in a measurement mode.

In a measurement mode, the contact pressure P is detected (S708).

The detected contact pressure is compared with the threshold contact pressure Pth (S710). If the detected contact pressure P is smaller than the threshold contact pressure Pth, a notice is given for a user to increase his contact pressure P (S712).

If the contact pressure P detected in operation S710 is larger than the threshold contact pressure Pth, the voltage drop V' across the voltage electrodes is measured (S714).

Then, the measured voltage drop V' is compensated for the threshold contact voltage Vth corresponding to the threshold contact pressure Pth (S716).

Then, a body fat value is calculated by using the compensated voltage (V=V'−Vth). Since the threshold contact pressure Pth can be different in every measurement try depending on the individual, it is preferable that the threshold contact pressure Pth is obtained in an experimental and statistical manner and then stored in a memory of the body fat measurement apparatus.

Figure 8:
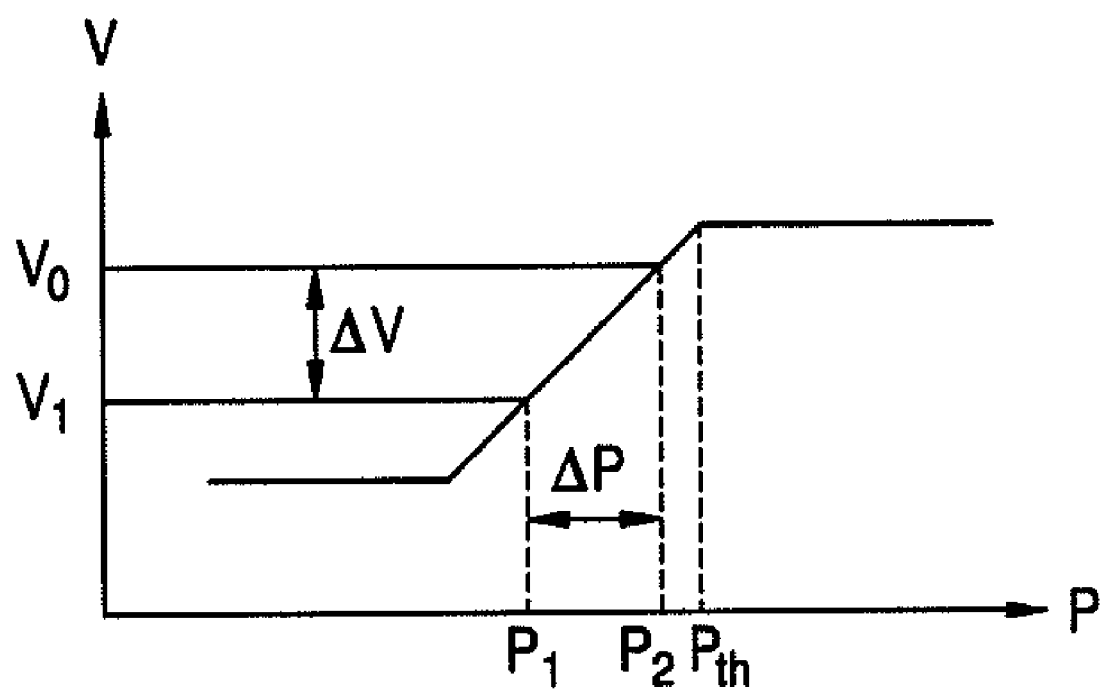
FIG. 8 schematically illustrates a principle of measuring body fat according to a third exemplary embodiment of the present invention.

FIG. 8 schematically illustrates a principle of measuring body fat according to the third embodiment of the present invention, which shows variation of the contact voltage depending on the contact pressure.

Referring to FIG. 8, the first and second conditional pressures P1 and P2 and the threshold contact pressure Pth are shown. The first and second conditional pressures P1 and P2 are selected from a range that the variation of the contact voltage is significant depending on the variation of the contact pressure (i.e., apparently linear range).

In a measurement mode, compensation for the contact voltage is accomplished by using interpolation. In this case, if the contact pressure is smaller than the threshold contact pressure Pth, the interpolation is used for the compensation.

However, if the contact pressure is larger than the threshold contact pressure Pth, the threshold contact voltage is used for the compensation.

Figure 9:
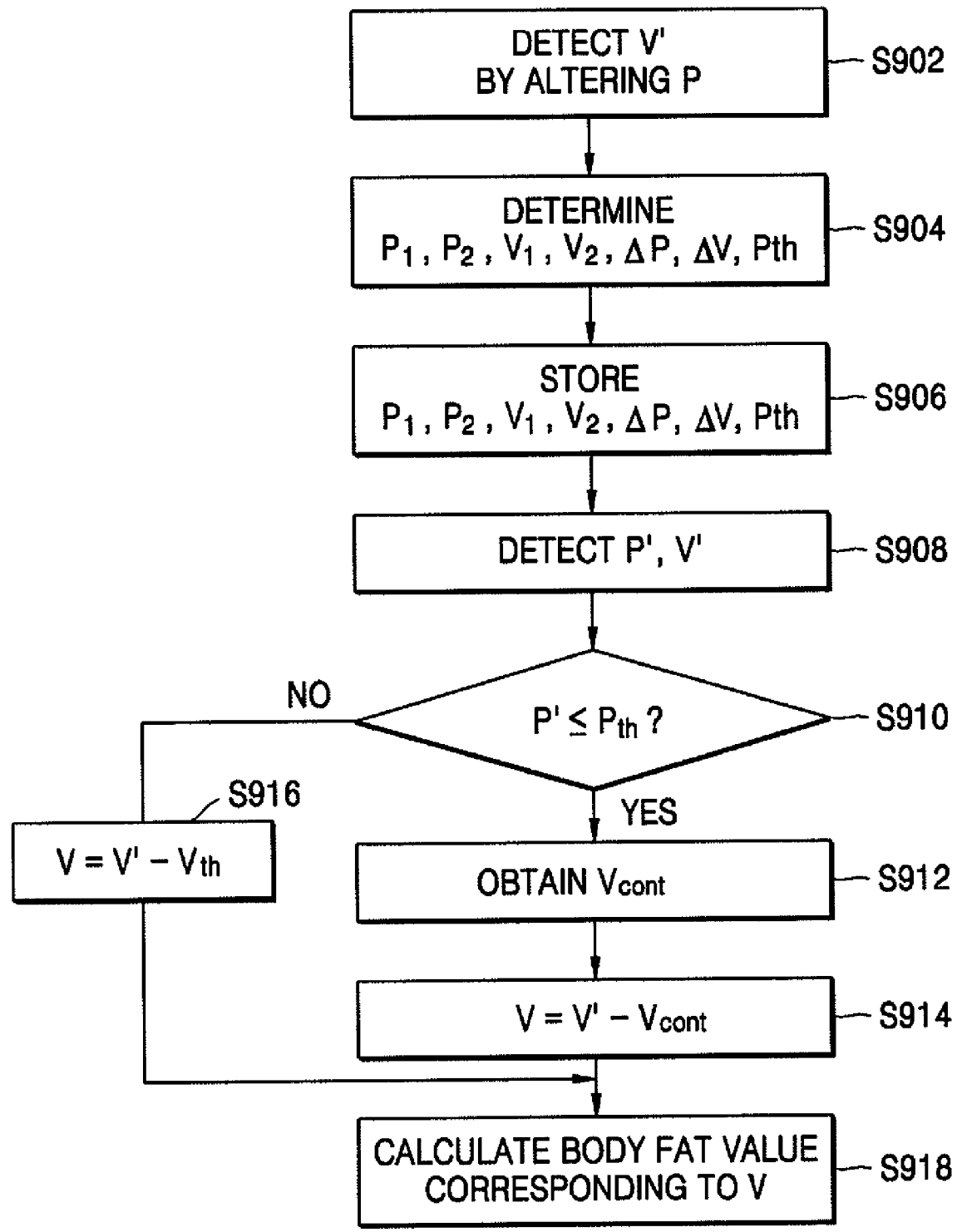
FIG. 9 is a flowchart illustrating a method of measuring body fat according to the third embodiment of the present invention.

FIG. 9 is a flowchart illustrating a method of measuring body fat according to the third embodiment of the present invention.

First, in a calibration mode, the voltage drop V' across the voltage electrodes is continuously detected by smoothly raising the contact pressure (S902).

A graph such as that shown in FIG. 8 is obtained by referring to variation of the detected voltage drop V' depending on the contact pressure, and the threshold contact pressure Pth, the conditional contact pressures P1 and P2, the difference ΔP between the conditional pressures P1 and P2, the conditional voltages V1 and V2, and the difference ΔV between the conditional voltages V1 and V2 are determined (S904).

The threshold contact pressure Pth, the conditional contact pressures P1 and P2, the difference ΔP between the conditional contact pressures P1 and P2, the conditional voltages V1 and V2, and the difference ΔV between the conditional voltages V1 and V2 are stored in a memory (S906).

In a measurement, the contact pressure P' and the voltage drop V' across the voltage electrodes are detected (S908).

In operation S910, the detected contact pressure P' is compared with the threshold contact pressure Pth.

If the detected contact pressure P' is smaller than the threshold contact pressure Pth, the contact voltage Vcont is calculated by interpolation (S912).

The measured voltage V' is compensated for by using the calculated contact voltage Vcont (S914).

If the contact pressure detected in operation S910 is larger than the threshold contact pressure Pth, the detected voltage drop V' is compensated for the threshold contact voltage Vth (S916).

Finally, a body fat value corresponding to the compensated voltage drop (V=V'−Vth) is calculated in operation (S918).

Figure 10:
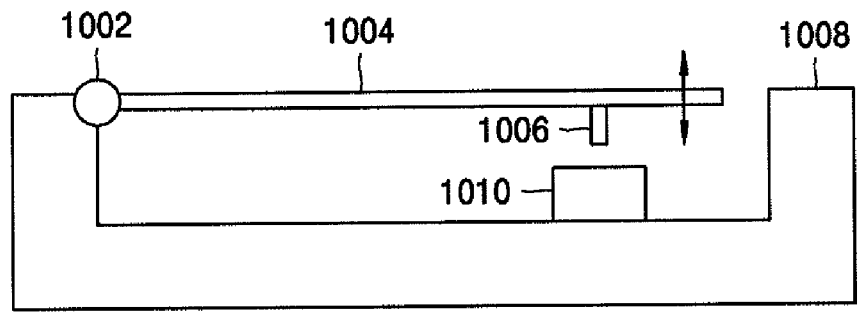
FIG. 10 illustrates a contact pressure detector used to measure a contact pressure according to an aspect of the present invention.

FIG. 10 illustrates a contact pressure detector 1000 used to measure a contact pressure according to an embodiment of the present invention. The contact pressure detector 1000 detects a contact pressure applied to the measurement electrodes, particularly, the voltage electrodes. The contact pressure detector 1000 includes a plate 1004 elastically supported by a hinge 1002, a first sensor 1006 mounted on the plate 1004, and a second sensor 1010 mounted on a frame 1008 and outputting a distance from the first sensor 1006. Preferably, but not necessarily, the plate 1004 is the voltage electrode.

When a contact pressure is applied, the plate 1004 moves in a downward direction against an elastic force of the hinge 1002. When the plate 1004 moves, the distance between the first and second sensors 1006 and 1010 is changed. Accordingly, a physical quantity proportional to the distance between the first and second sensors 1006 and 1010, i.e., a value corresponding to the contact pressure is obtained.

Figure 11A:
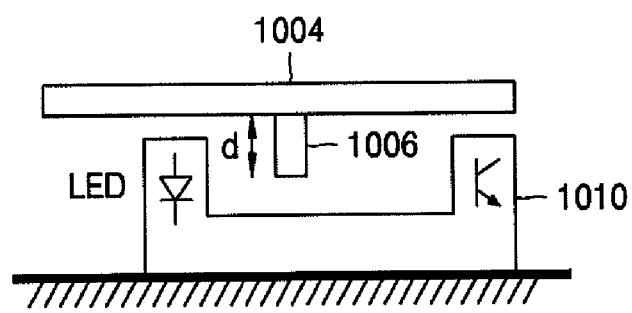
FIGS. 11A through 11C illustrate exemplary constructions of the first and second sensors shown in FIG. 10.
Figure 11B:
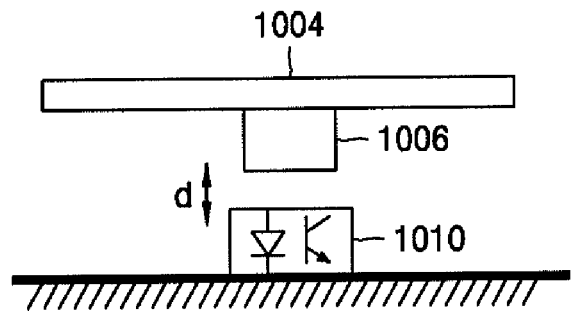
Figure 11C:
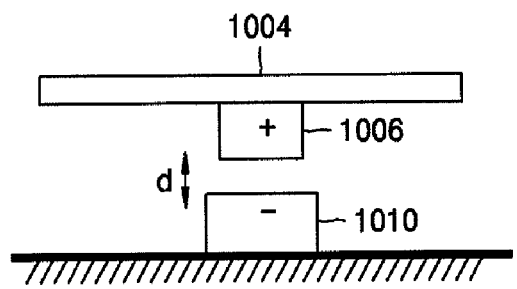

FIGS. 11A through 11C illustrate exemplary constructions of the first and second sensors 1006 and 1010 shown in FIG. 10. Specifically, FIG. 11A shows a transmissive photo-interrupter, FIG. 11B shows a reflective photo-interrupter, and FIG. 11C shows a capacitive sensor.

Figure 1:
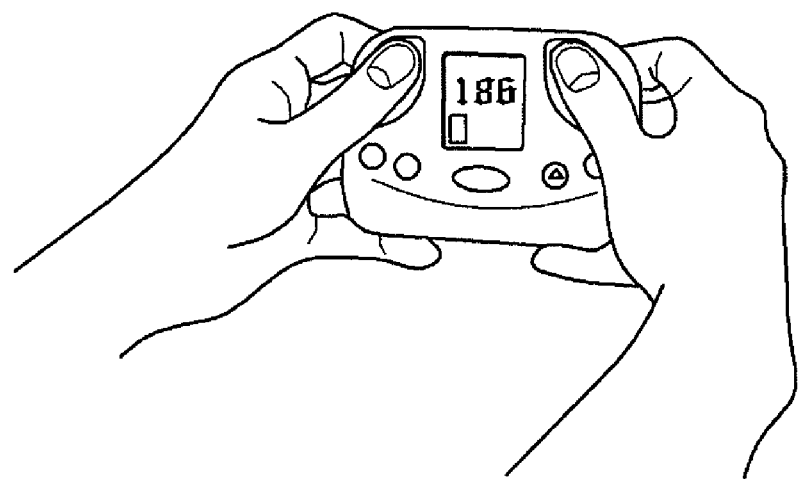
FIG. 1 schematically illustrates an example of a portable body fat measurement apparatus.
Figure 2:
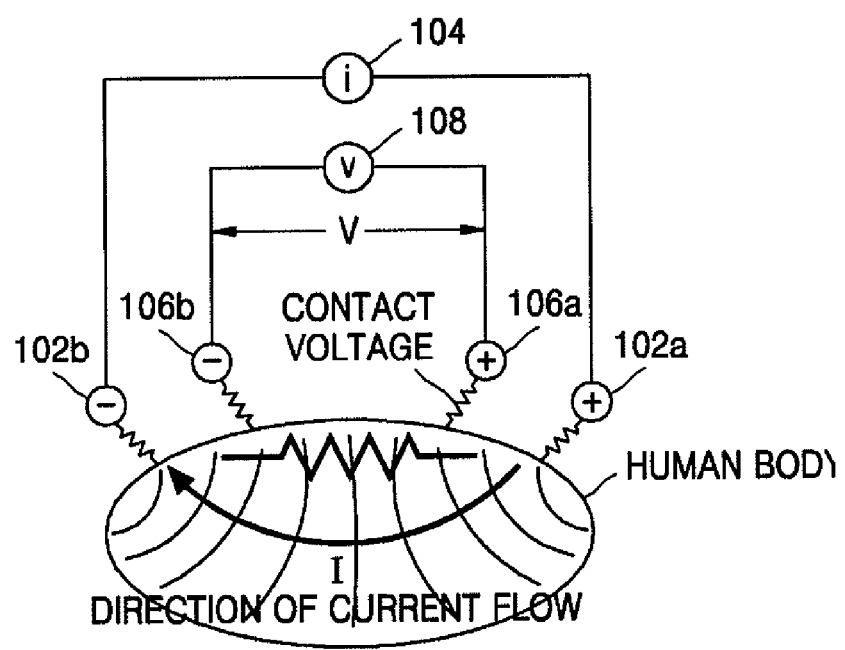
FIG. 2 schematically illustrates a principle of measuring body fat by using a four-electrode type body fat measurement apparatus.
Figure 3:
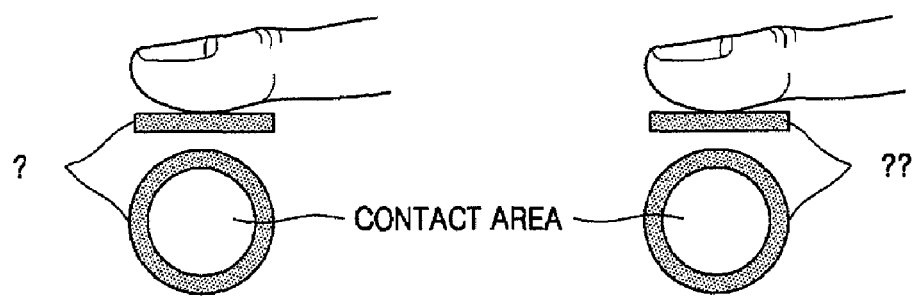
FIG. 3 schematically illustrates variation of a body fat value depending on the contact area.
Figure 12:
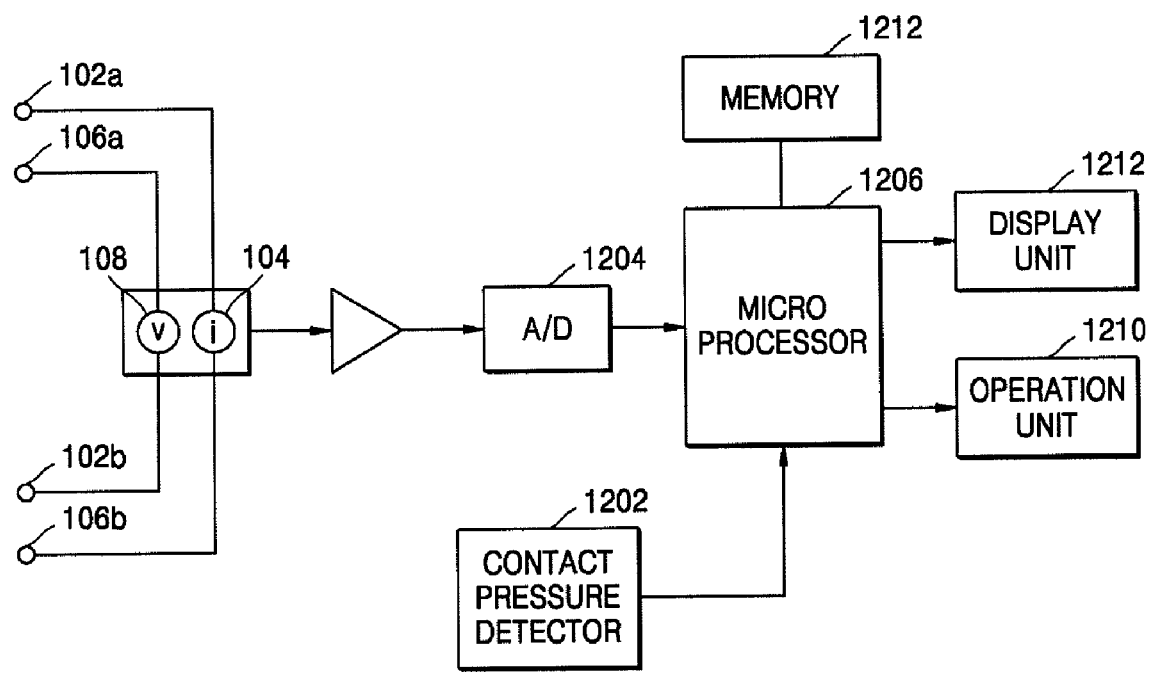
FIG. 12 is a block diagram illustrating a body fat measurement apparatus according to an aspect of the present invention.

FIG. 12 is a block diagram illustrating a body fat measurement apparatus according to an embodiment of the present invention. The body fat measurement apparatus 1200 shown in FIG. 12 includes a contact pressure detector 1202, an analog/digital (A/D) converter 1204, a microprocessor 1206, a display unit 1208, an operation unit 1210, and a memory 1212. Since the current electrodes 102a and 102b, the voltage electrodes 106a and 106b, the constant current source 104, and the voltage meter 108 have been already illustrated and described in connection with FIG. 2, their detailed descriptions are not repeated.

The contact pressure detector 1202 is to detect the contact pressure, and, for example, one of those shown in FIGS. 10, and 11A through 11C can be employed.

The A/D converter 1204 converts the voltage detected in the voltage detector 108 into a digital value and then provides it to the microprocessor 1206.

The microprocessor 1206 controls operations of the body fat measurement apparatus 1200 to perform, for example, a method of measuring body fat according to the present invention. In a calibration mode, the microprocessor 1206 informs a user of the progress of procedures through the display unit 1208 or instructs required operations. Also, the microprocessor receives the contact pressure detected through the contact pressure detector 1202 and the measurement values through the A/D converter 1204, and calculates the threshold contact pressure and parameters required for the interpolation. Then, they are stored in the memory 1212.

In a measurement mode, the microprocessor 1206 receives the contact pressure detected through the contact pressure detector 1202 and measurement values through the A/D converter 1204. Also, the microprocessor 1206 processes measurement values by compensating for the contact pressure with reference to the parameters necessary for the interpolation and the threshold contact pressure stored in the memory 1212, or notifies a user to retain a proper contact pressure through the display unit 1208.

The microprocessor 1206 controls both the calibration mode and the measurement mode according to the processes shown in FIG. 5 in connection with the first embodiment, the processes shown in FIG. 7 in connection with the second embodiment, or the processes shown in FIG. 9 in connection with the third embodiment.

In the body fat measurement apparatus shown in FIG. 12, the contact pressure is detected through the contact pressure detector 1202 and the contact voltage caused by the contact pressure during an actual measurement are compensated by using the values measured under the conditional pressures.

Therefore, it is possible to provide body fat measurement results having little measurement errors and high repeatability.

Also, in the body fat measurement apparatus shown in FIG. 12, the threshold contact pressure is calculated, and a user is induced to retain his contact pressure above the threshold contact pressure. Therefore, it is possible to provide a more accurate measurement result.

According to the present invention, the contact voltage caused by the contact pressure is compensated by using the values measured under the conditional pressures. Therefore, it is possible to provide body fat measurement results having little error and high repeatability.

In addition, the threshold contact pressure is obtained, and a user is induced to retain his contact pressure above the threshold contact pressure. Therefore, it is possible to provide more accurate measurement results.

While the present invention has been particularly shown and described with reference to exemplary embodiments thereof, it will be understood by those skilled in the art that various changes in form and details may be made therein without departing from the spirit and scope of the invention as defined by the appended claims. The exemplary embodiments should be considered in a descriptive sense only and not for purposes of limitation. Therefore, the scope of the invention is defined not by the detailed description of the invention but by the appended claims, and all differences within the scope will be construed as being included in the present invention.

What is claimed is:

1. A method of measuring body fat by using current electrodes for applying a constant current in a human body and voltage electrodes for detecting a voltage drop caused by bioelectrical impedance of the human body, the method comprising:

continually detecting a voltage drop across the voltage electrodes by smoothly raising a contact pressure applied to the electrodes;

determining a threshold contact pressure with reference to the detected voltage drop depending on variation of the contact pressure, the voltage drop across the voltage electrodes not increasing under the threshold contact pressure even when the contact pressure increases;

comparing a detected contact pressure with the threshold contact pressure;

detecting a measurement voltage across the voltage electrodes only when the detected contact pressure is larger than the threshold contact pressure; and compensating the measurement voltage for a threshold contact voltage corresponding to the threshold contact pressure and calculating a body fat value corresponding to the compensated measurement voltage.

2. The method according to claim 1, further comprising inducing a user to increase his contact pressure if the detected contact pressure is smaller than the threshold contact pressure.

3. An apparatus for measuring body fat by using current electrodes for applying a constant current in a human body and voltage electrodes for detecting a voltage drop caused by bioelectrical impedance of the human body, the apparatus comprising:

a contact pressure detector detecting a contact voltage applied to the voltage electrodes;

a voltage meter measuring a voltage drop across the voltage electrodes; and a microprocessor continually detecting a voltage drop across the voltage electrodes by smoothly raising the contact pressure applied to the voltage electrodes through the contact pressure detector and the voltage meter;

determining a threshold contact pressure with reference to the detected voltage drop depending on variation of the contact pressure, the voltage drop across the voltage electrodes not increasing under the threshold contact pressure even when the contact pressure increases;

comparing a detected contact pressure with the threshold contact pressure;

detecting a measurement voltage across the voltage electrodes only when the detected contact pressure is larger than the threshold contact pressure;

compensating the measurement voltage for a threshold contact voltage corresponding to the threshold contact pressure; and calculating a body fat value corresponding to the compensated measurement voltage.

4. The apparatus according to claim 3, wherein the microprocessor induces a user to raise his contact pressure if the detected contact pressure is smaller than the threshold contact pressure.

* * * * *